US011458070B2

(12) United States Patent
Roura Fernandez et al.

(10) Patent No.: US 11,458,070 B2
(45) Date of Patent: *Oct. 4, 2022

(54) CONTAINER FOR A SOLUTION OF HUMAN PLASMA PROTEINS AND METHOD FOR OBTAINING THEREOF

(71) Applicant: GRIFOLS, S.A., Barcelona (ES)

(72) Inventors: Carlos Roura Fernandez, San Juan Despi (ES); Jose Antonio Garcia Garcia, Las Torres Cotillas (ES); Estela Llorens Masas, Parets del Valles (ES); Nuria Marzo Adam, Parets del Valles (ES)

(73) Assignee: GRIFOLS, S.A., Barcelona (ES)

( * ) Notice: Subject to any disclaimer, the term of this patent is extended or adjusted under 35 U.S.C. 154(b) by 399 days.

This patent is subject to a terminal disclaimer.

(21) Appl. No.: 16/814,895

(22) Filed: Mar. 10, 2020

(65) Prior Publication Data

US 2020/0206080 A1 Jul. 2, 2020

Related U.S. Application Data

(63) Continuation of application No. 15/611,582, filed on Jun. 1, 2017.

(30) Foreign Application Priority Data

Sep. 16, 2016 (ES) ............................... ES201631198

(51) Int. Cl.
*A61J 1/10* (2006.01)
*B32B 27/08* (2006.01)
(Continued)

(52) U.S. Cl.
CPC ............... *A61J 1/10* (2013.01); *A61J 1/1431* (2015.05); *A61J 1/1468* (2015.05); *A61J 1/2048* (2015.05);
(Continued)

(58) Field of Classification Search
CPC ....................................................... A61J 1/10
See application file for complete search history.

(56) References Cited

U.S. PATENT DOCUMENTS

| 7,476,428 B2 * | 1/2009 | Burki ...................... B32B 27/32 |
| | | 428/34.7 |
| 2005/0255200 A1 * | 11/2005 | Takahagi ............. B65D 77/225 |
| | | 426/113 |

(Continued)

FOREIGN PATENT DOCUMENTS

| EP | 1 245 217 A2 | 10/2002 |
| EP | 1 245 217 A3 | 1/2004 |

(Continued)

OTHER PUBLICATIONS

European Search Report, dated Dec. 7, 2017, in European Patent Application No. 17382322.0.

(Continued)

*Primary Examiner* — Jessica R Arble
(74) *Attorney, Agent, or Firm* — Knobbe, Martens Olson & Bear LLP (57) ABSTRACT

A container for a solution of human plasma proteins has a primary inner bag made up of a first multilayer polymer film with two outer layers of polyethylene (PE) and an intermediate layer of ethylene vinyl alcohol (EVOH) copolymer, and a secondary outer bag made up of a second multilayer film with layers of polyethylene terephthalate (PET)-silicon oxides (SiOx), oriented polyamide (OPA), polypropylene (PP)-silicon oxides (SiOx) and polypropylene (PP), referred to as multilayer PP-SiOx.

1 Claim, 7 Drawing Sheets

(51) Int. Cl.
*B65B 7/02* (2006.01)
*B65D 77/04* (2006.01)
*B65D 81/24* (2006.01)
*A61J 1/14* (2006.01)
*A61J 1/20* (2006.01)
*A61K 38/38* (2006.01)
*B65B 3/00* (2006.01)
*B65B 63/08* (2006.01)
*B65D 65/40* (2006.01)
*B65D 75/58* (2006.01)
*C07K 16/00* (2006.01)

(52) U.S. Cl.
CPC .............. *A61K 38/38* (2013.01); *B32B 27/08* (2013.01); *B65B 3/003* (2013.01); *B65B 7/02* (2013.01); *B65B 63/08* (2013.01); *B65D 65/40* (2013.01); *B65D 75/5855* (2013.01); *B65D 77/04* (2013.01); *B65D 81/24* (2013.01); *C07K 16/00* (2013.01)

(56) References Cited

U.S. PATENT DOCUMENTS

| | | |
|---|---|---|
| 2007/0071925 A1 | 3/2007 | Smith et al. |
| 2008/0008848 A1 | 1/2008 | Dick et al. |
| 2013/0049356 A1 | 2/2013 | Pittet et al. |
| 2013/0327677 A1* | 12/2013 | McDorman ............ B65D 25/00 206/524.2 |
| 2014/0004284 A1 | 1/2014 | Inaba et al. |
| 2015/0298888 A1 | 10/2015 | Kuhn et al. |
| 2016/0368257 A1* | 12/2016 | Blackman ............... B32B 27/08 |

FOREIGN PATENT DOCUMENTS

| | | |
|---|---|---|
| EP | 1894851 A1 | 3/2008 |
| EP | 2965907 A1 | 1/2016 |
| EP | 3 011 944 A1 | 4/2016 |
| ES | P 201431561 | 10/2014 |
| JP | 2009132431 A | 6/2009 |
| WO | WO 2002/085111 A1 | 10/2002 |
| WO | WO 2007/038968 A1 | 4/2007 |
| WO | WO 2009/082133 A2 | 7/2009 |

OTHER PUBLICATIONS

Spanish Search Report, dated Feb. 7, 2017, in Spanish Application No. 201631198.
English Translation of JP 2009132431 A.

* cited by examiner

CONTAINER FOR A SOLUTION OF HUMAN PLASMA PROTEINS AND METHOD FOR OBTAINING THEREOF

PRIORITY AND CROSS-REFERENCE TO RELATED APPLICATIONS

This application is a Continuation Application of U.S. application Ser. No. 15/611,582, filed Jun. 1, 2017, which claims the benefit of Spanish Application No. P 201631198, filed on Sep. 16, 2016, which are hereby incorporated by reference in their entirety.

BACKGROUND

Field

The present invention relates to the sector for the production of haemoderivative products, specifically to the preparation of human plasma proteins for therapeutic use. More specifically, the present invention relates to a container made up of two bags made of plastics material, that is, a primary inner bag which contains a solution of human plasma proteins for therapeutic use and a secondary bag outside said primary bag. The present invention also relates to the method of preparing said container.

Description of the Related Art

Usually, in the pharmaceutical industry in general and in the industry relating to products obtained from human plasma in particular, glass receptacles or vials are used as the end packaging of the therapeutic product. Glass has the advantages of being generally inert to contact with the pharmaceutical compound; it is temperature-resistant, facilitating sterilisation, and it is transparent, impermeable to gases, easy to clean, does not deteriorate over time, and the hardness thereof helps preserve the integrity of said receptacles. Said properties, among others, mean that glass is the preferred raw material in said industry for containing the end product.

Recently, it has been found that receptacles made of plastics material, in particular flexible bags made of plastics material, are also useful as the end packaging of haemoderivative products for various reasons: said bags are easy to shape, which gives them great versatility and adaptability in design, they are resistant to breakage, ergonomic, and owing to their low density and weight provide significant savings in transport and logistics costs. Moreover, said bags are flexible and easy to handle, which is why they are in demand in the public health sector. Another advantage of bags made of plastics material is that they are compatible with sterilisation by radiation, either by gamma rays or electron beams (e-beams). At present, solutions of haemoderivative products are available on the market sold in bags made of plastics material, for example, Flexbumin®, which is a 25% solution of human plasma albumin, marketed by Baxalta Spain S.L.

However, flexible bags made of plastics material have drawbacks related to the fact that the majority of the plastics materials used are permeable to gases such as the water vapor, oxygen and carbon dioxide present in the atmosphere. Said transmission of gases, vapors or liquids through the plastics material may have a negative effect on the useful life of the medicinal product. For example, said transmission may alter the properties of the product, and also the organoleptic characteristics thereof, as well as the color. Furthermore, temperature and humidity are important factors which influence the permeability of oxygen and water through the plastics material. A rise in temperature produces an increase in permeability to gases. Sensitivity to oxygen and other gases may be higher or lower depending on the protein, duration and conditions of storage.

There is therefore still a need for containers made of plastics material, particularly flexible bags made of plastics material, which preserve the pharmaceutical compounds, especially for sensitive proteins, without changing the properties thereof, ensure that a barrier is created to gases such as water vapor or oxygen, have a design which favors aseptic filling, are compatible with sterilisation, and ensure the integrity of the receptacle, while retaining their flexibility.

In the specific case of liquid solutions of human plasma immunoglobulins, the European Pharmacopoeia requires that said solutions must be clear and of a pale yellow to light brown color. However, the present inventors have noted that if an immunoglobulin solution is stored for some months in a bag made of plastics material, the receptacle is subject to weight loss owing to the semi-permeability of the plastics material and the solution becomes a yellow-brown color, which renders said solution unacceptable for therapeutic use in humans.

In the prior art, various ways are known of overcoming the above-mentioned problems of bags made of plastics material. For example, the plasma solutions may be stored in a dark environment at low temperature (5° C.), and atmospheric gases may be removed with inert gases, such as nitrogen. However, all entail increased difficulty in the methods of obtaining and storing said products, including a rise in the costs of obtaining said products

SUMMARY

The inventors have therefore developed a container for solutions of human plasma proteins which, surprisingly, overcomes the drawbacks of the containers of the prior art. The container of the present invention is made up of a primary inner bag and a secondary outer bag. The primary bag is the one which is in direct contact with the product, or rather, with the solution of human plasma proteins, while the secondary bag is in contact with the outer portion of the primary bag. In other words, the present invention is based on the surprising discovery of a specific combination of the materials of the primary and secondary bags which means that in said container the human plasma proteins, such as albumin or immunoglobulins among others, can be stored with a significant reduction in the weight lost by the container compared with the same primary bag when a secondary bag is not used and, in addition, in the specific case of immunoglobulins, stable coloration of the solution is obtained when stored for at least three months.

In the container according to the present invention, the primary bag is made up of a multilayer polymer film in which there are three main layers: two layers of polyethylene (PE) on the outer sides and an intermediate layer of ethylene vinyl alcohol (EVOH) copolymer. A very suitable material for the primary bag of the present invention is that marketed under the name SOLMED Infuflex 9101 (Renolit, Netherlands).

The primary bag of the container of the present invention comprises an inlet/cap structure, as described in Spanish patent application no. 201431561. That is to say, an inlet/cap structure which has two closure positions, in which the first closure position consists of a reversible hermetic closure and the second closure position consists of a final or irreversible hermetic closure by welding. This type of inlet/cap structure allows contamination of the pharmaceutical compound to be avoided during the process of aseptically filling the primary bag with said pharmaceutical compound, for example, biological contamination and/or contamination by particles resulting from the welding process.

In the container of the present invention, the secondary bag is made up of a multilayer film formed by layers of polyethylene terephthalate (PET)-silicon oxides ($SiO_x$), oriented polyamide (OPA), polypropylene (PP)-silicon oxides ($SiO_x$) and polypropylene (PP), such as that marketed under the name MEDIFLEX (Amcor, Belgium), referred to generically herein as 'multilayer PP-SiOx'. This type of secondary bag represents a barrier to water and oxygen, is transparent and compatible with sterilisation.

Moreover the secondary bag provides abrasion protection and identification information for the product within the primary inner bag, keeps the primary inner bag clean, and can be designed in peelable form, that is, that can be broken manually without the need for cutting implements in order to access the primary bag.

Thus, in a first aspect, the present invention discloses a container characterized in that it comprises: a) a primary inner bag which comprises a solution of human plasma proteins, of which the primary bag is made up of a multilayer polymer film in which two outer layers of polyethylene (PE) and an intermediate layer of ethylene vinyl alcohol (EVOH) copolymer are present and b) a secondary outer bag made up of a multilayer film which has layers of polyethylene terephthalate (PET)-silicon oxides (SiOx), oriented polyamide (OPA), polypropylene (PP)-silicon oxides (SiOx) and polypropylene (PP).

The primary bag of the present invention may comprise an inlet/cap structure or connector which has two closure positions, in which the first closure position consists of a reversible hermetic closure and the second closure position consists of a final or irreversible hermetic closure by welding. Moreover, the primary bag is formed by welding said connector to the sheets of the side walls, thus defining the geometry of the bag.

One of the problems which appear in welding bags by heat contact is when heat is applied to produce the weld between the sheets and the inlet using hot moulds. It is possible that the heat, which takes time to reach the inside of the inlet since it is applied through the sheet, has the unwanted effect of degrading the sheet without adequately heating the material of the inlet and thus without producing a weld of the required quality. This effect is particularly significant in the zone in which the flat weld of the bag is connected to the circular weld of the inlet, giving rise to sealing loss, which is commonly known as 'side channel' leakage.

To overcome this problem, the primary bag of the present invention has an inlet with two small wings, the small thickness of which facilitates the heating and welding thereof. In addition, a pre-heating station for the inlet can be provided on the welding machine, so that the material arrives at the welding station in a state close to melting and it will therefore not be necessary to apply a great deal of thermal energy through the bag in order to achieve a quality weld.

Furthermore, the cap or 'twist-off' valve with which the bag is closed after filling also has the function of providing access to the bag by means of a punch at the moment the medicinal product is administered to the patient. Punches usually have standardised general dimensions which define the conicity at the end thereof, although each manufacturer has small variations in measurements.

There is therefore a need to achieve a compromise between having sufficient interference between the punch and the valve to achieve a hermetic closure. In particular, it must be ensured that not much force is required when introducing the punch, and that there is sufficient residual resistance to ensure that the punch cannot be withdrawn accidentally by a sudden movement during administration of the medicinal product. In addition to all of this, it must be able to adapt to the different models of punch on the market.

As a solution to the above problem, an inner toric protrusion has been designed on the valve, at a distance from the valve membrane that ensures that when the end of the punch begins to perforate the membrane, there is a hermetic fit between the punch and the toric protrusion. Because it is isolated, said protrusion allows for a good fit, without the need for great force when completing the introduction of the punch, and said fit is maintained for the time of administration.

In a preferred embodiment, the human plasma proteins which the inner bag contains are albumin, α-1-antitrypsin, von Willebrand factor, coagulation factors such as factor VII, factor VIII and factor IX, immunoglobulins, plasminogen, plasmin, antithrombin III, fibrinogen, fibrin, thrombin or combinations thereof, obtained from human plasma. It is also envisaged that said proteins may not be of biological origin, but may be obtained by any other process or method known in the prior art, for example, chemical synthesis, recombinant production or transgenic production. In a more preferred embodiment, the human plasma proteins are albumin and immunoglobulins. In the most preferred embodiment they are immunoglobulins.

In a preferred embodiment, the welding of the cap to the inlet of the container of the present invention is produced by ultrasound. In another preferred embodiment, the welding of the connector to the inner bag is produced by heat contact.

In another preferred embodiment, the secondary bag of the present invention is designed in peelable form, that is, which can be broken manually without the need to use cutting implements to access the primary bag.

The present invention also relates to a method of preparing the above-mentioned container. Said method is characterized in that it comprises the following steps:
a) sterile filtering of the solution of human plasma proteins through a 0.2 μm membrane;
b) filling the primary bag by lifting the cap of said inner bag in a sterile environment and introducing the sterile solution obtained at step a);
c) inserting the cap into the inlet of the primary bag in a sterile environment, providing a hermetic closure therebetween by welding;
d) inserting the primary bag obtained at step c) into the secondary bag and welding said secondary bag.

With the method of the present invention the conditions of sterility and asepsis of the primary bag, and thus of the contents thereof, are maintained. The primary bags which have been filled at step b) have been previously sterilised by gamma radiation or electron beam (e-beam) radiation.

As mentioned earlier, in a preferred embodiment, the human plasma proteins contained in the inner bag are albumin, α-1-antitrypsin, von Willebrand factor, coagulation factors such as factor VII, factor VIII and factor IX, immunoglobulins, plasminogen, plasmin, antithrombin III, fibrinogen, fibrin, thrombin or combinations thereof, obtained from human plasma. It is also envisaged that said proteins may not be of biological origin, but may be obtained by any other process or method known in the prior art, for example, chemical synthesis, recombinant production or transgenic production. In a more preferred embodiment, the human plasma proteins are albumin and immunoglobulins. In the most preferred embodiment said proteins are immunoglobulins.

Optionally, if the human plasma proteins are immunoglobulins, the method of the present invention comprises an additional incubation step maintaining conditions equivalent to those of the industrial process, that is, for 21 days at 25±2° C.

BRIEF DESCRIPTION OF THE DRAWINGS

For a better understanding, the present invention is described below with reference to the accompanying drawings, which are presented as an example and which in no case are intended to limit the present invention. Equivalent or similar structures between the different figures have been designated with the same numeral.

DETAILED DESCRIPTION

Figure 1:
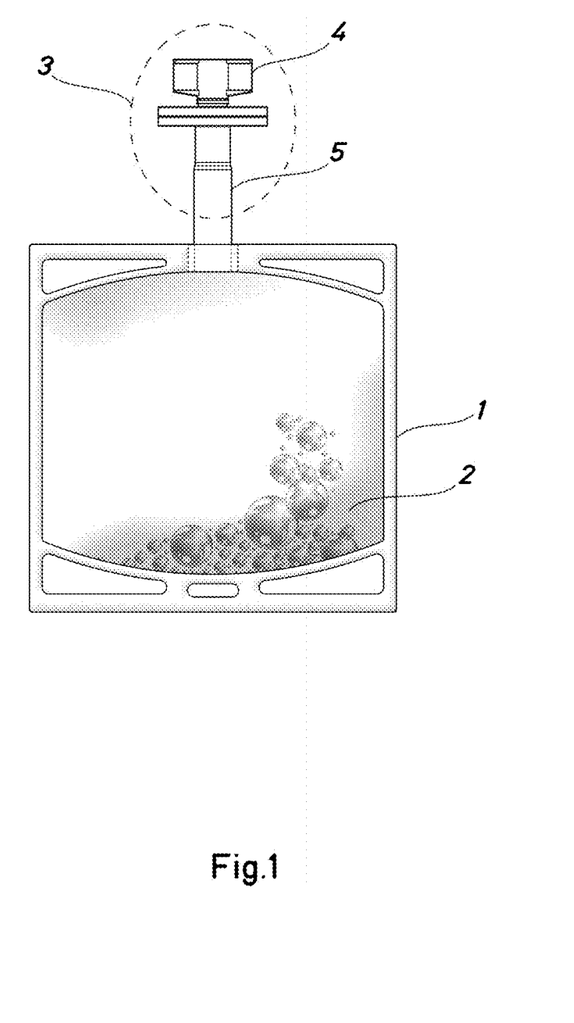
FIG. 1 is a front view of an embodiment of the primary bag of the container of the present invention filled with a solution of human plasma protein.

As mentioned previously, FIG. 1 is a front view of an embodiment of the primary bag of the present invention. Said figure shows a container -1- which contains a solution of human plasma proteins -2-, said container comprising an inlet/cap structure -3- made up of a cap -4- and an inlet -5-. Said cap -4- is inserted into said inlet -5-, providing a hermetic closure of the container -1-.

Figure 2:
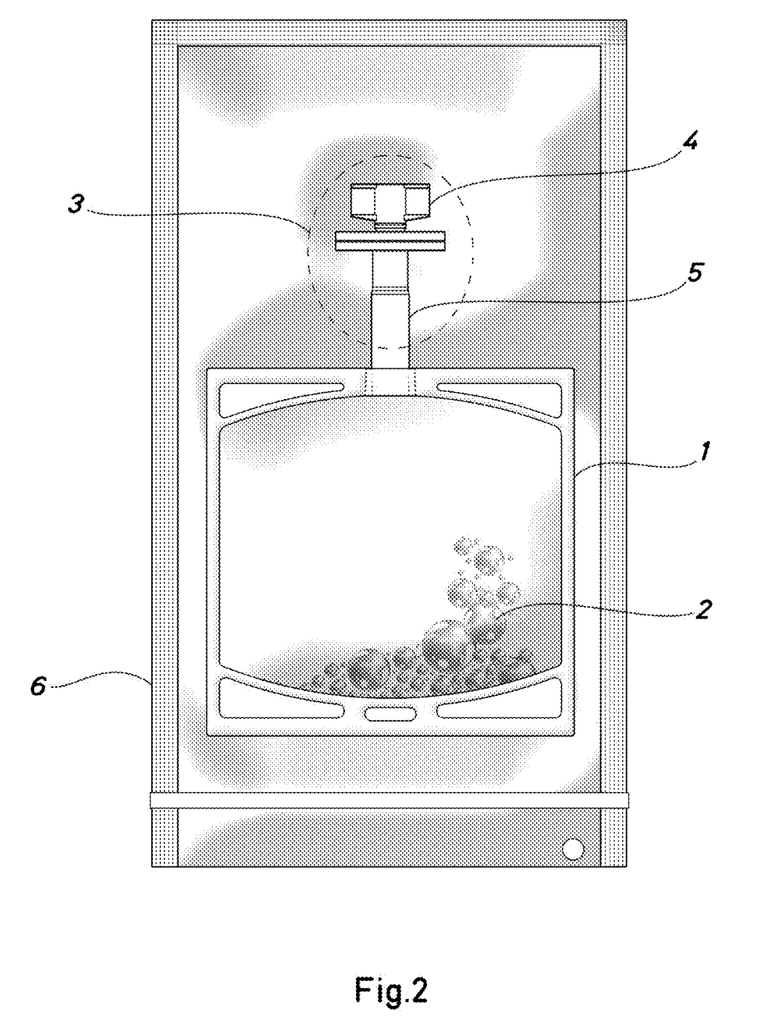
FIG. 2 is an embodiment of the container of the present invention.

FIG. 2 is a front view of an embodiment of the container of the present invention. Said system is made up of a primary bag -1-, similar to that described in FIG. 1, and a secondary bag -6-, which contains said first bag -1-. Said primary bag -1- contains a solution of human plasma proteins -2-, and comprises an inlet/cap structure -3- made up of a cap -4- and an inlet -5-.

Figure 3:
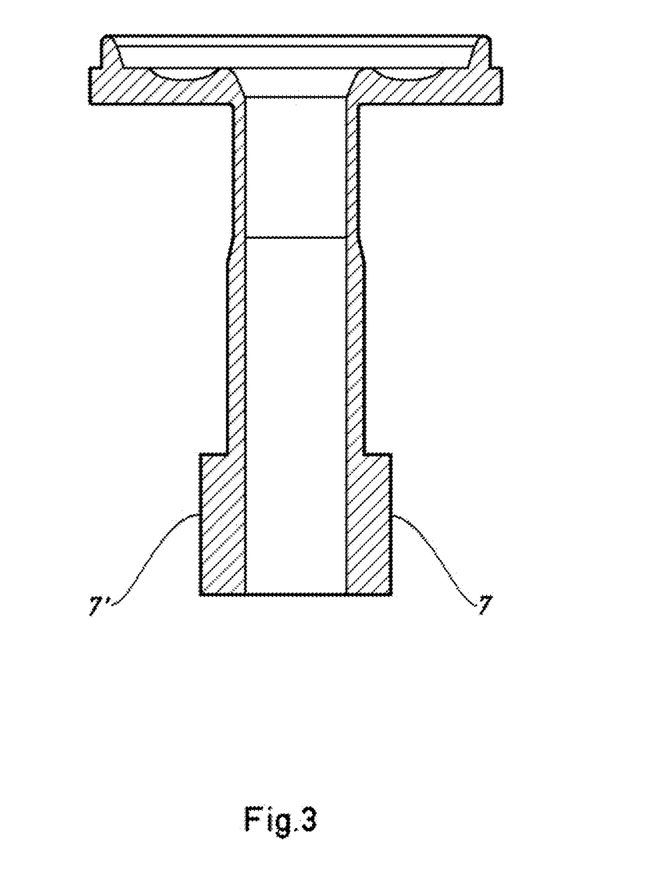
FIG. 3 is a cross section of the inlet of the primary bag of the container of the present invention.

FIG. 3 is a cross section of the inlet of the primary bag of the container of the present invention. As can be seen, said inlet comprises some small wings -7-, -7'-, which facilitate the heating and welding thereof to the sheets of the primary bag.

Figure 4:
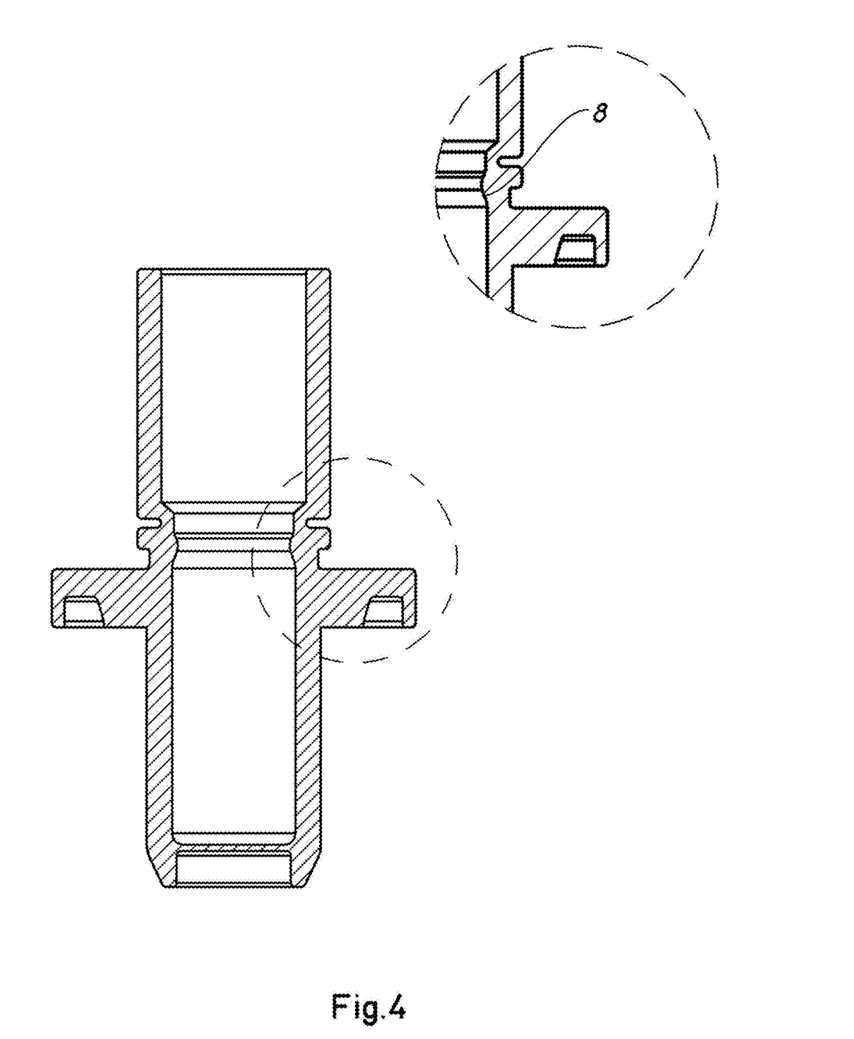
FIG. 4 is a cross section of the cap of the primary bag of the container of the present invention.

Furthermore, FIG. 4 is a cross section of the cap of the primary bag of the container of the present invention. Said cap has a toric protrusion -8- at a distance from the valve membrane that ensures that when the end of the punch begins to perforate the membrane, for example during administration of the medicinal product to a patient, there is a hermetic fit between the punch and the toric protrusion, ensuring the seal of said primary bag.

EXAMPLES

Example 1. Accelerated Stability Study of a Primary Bag which Contains Albumin, with and without a Secondary Outer Bag Four primary bags of different volumes (50, 100, 250 and 500 ml) were prepared, made up of a material composed of three layers of polymer: two layers of polyethylene (PE) on the outer sides and an intermediate layer of ethylene vinyl alcohol (EVOH) copolymer (SOLMED Infuflex 9101, Renolit), with a 20% solution of human plasma albumin. Said primary bags were inserted into secondary bags made of different materials: 150 µm thick polypropylene (PP), 300 µm thick polypropylene (PP) and 140 µm thick polypropylene coated with silicon oxides (multilayer PP-SiOx) (MEDI-FLEX, Amcor, Belgium). One primary bag was not placed inside a secondary bag. All the containers and the primary bag without a secondary bag were kept for 12 months at 40° C. and at the end of this time the weight loss of the container and the bag was determined expressed as a percentage (%).

The results can be seen in FIG. 3. A reduction was observed in the weight loss of the primary bags which were placed in secondary bags, the greatest reduction being in the case of the secondary bag of multilayer PP-SiOx (MEDIFLEX, Amcor, Belgium).

Example 2. Stability Study of a Primary Bag which Contains Albumin, with and without a Secondary Bag Containers prepared in the same way as in example 1 were kept for 12 months at 5° C. and at the end of that time the weight loss of each container was determined expressed as a percentage (%).

The results can be seen in FIG. 4. As with example 1, a reduction is observed in the weight loss of the primary bags which were placed inside secondary bags, the greatest reduction being in the case of the secondary bag made of multilayer PP-SiOx (MEDIFLEX, Amcor, Belgium).

Example 3. Stability Study of a Primary Bag which Contains Albumin, with Secondary Bags Made of Different Types of Coated Polypropylene Two primary bags of different volumes (50 and 100 ml) were prepared, made up of a material composed of three layers of polymer: two layers of polyethylene (PE) on the outer sides and an intermediate layer of ethylene vinyl alcohol (EVOH) copolymer (SOLMED Infuflex 9101, Renolit), with a 20% solution of human plasma albumin. Said primary bags were inserted into secondary bags made of two different materials: polypropylene coated with silicon oxides (multilayer PP-SiOx) (MEDIFLEX, Amcor, Belgium) and 140 μm thick polypropylene coated with aluminium oxides (PP-AlOx). All the prepared containers were kept for two months at 40° C. and at the end of that time the weight loss of the container was determined expressed as a percentage (%).

Figure 5:
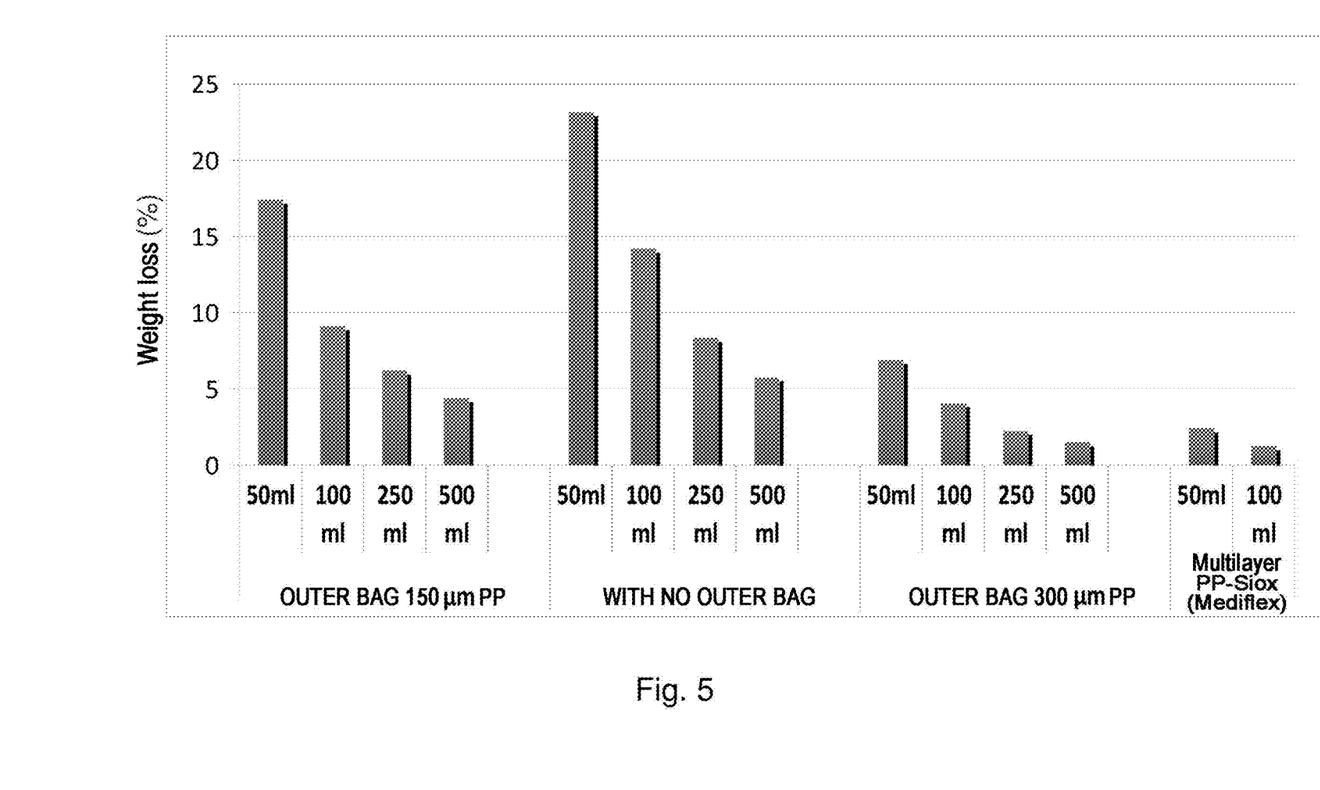
FIG. 5 shows the results for weight loss in an accelerated stability study (12 months at 40° C.) of a primary bag which contains a solution of human plasma albumin without a secondary bag and with different secondary containers: 150 µm thick polypropylene (PP), 300 µm thick polypropylene (PP) and polypropylene coated with silicon oxides (multilayer PP-SiOx).
Figure 6:
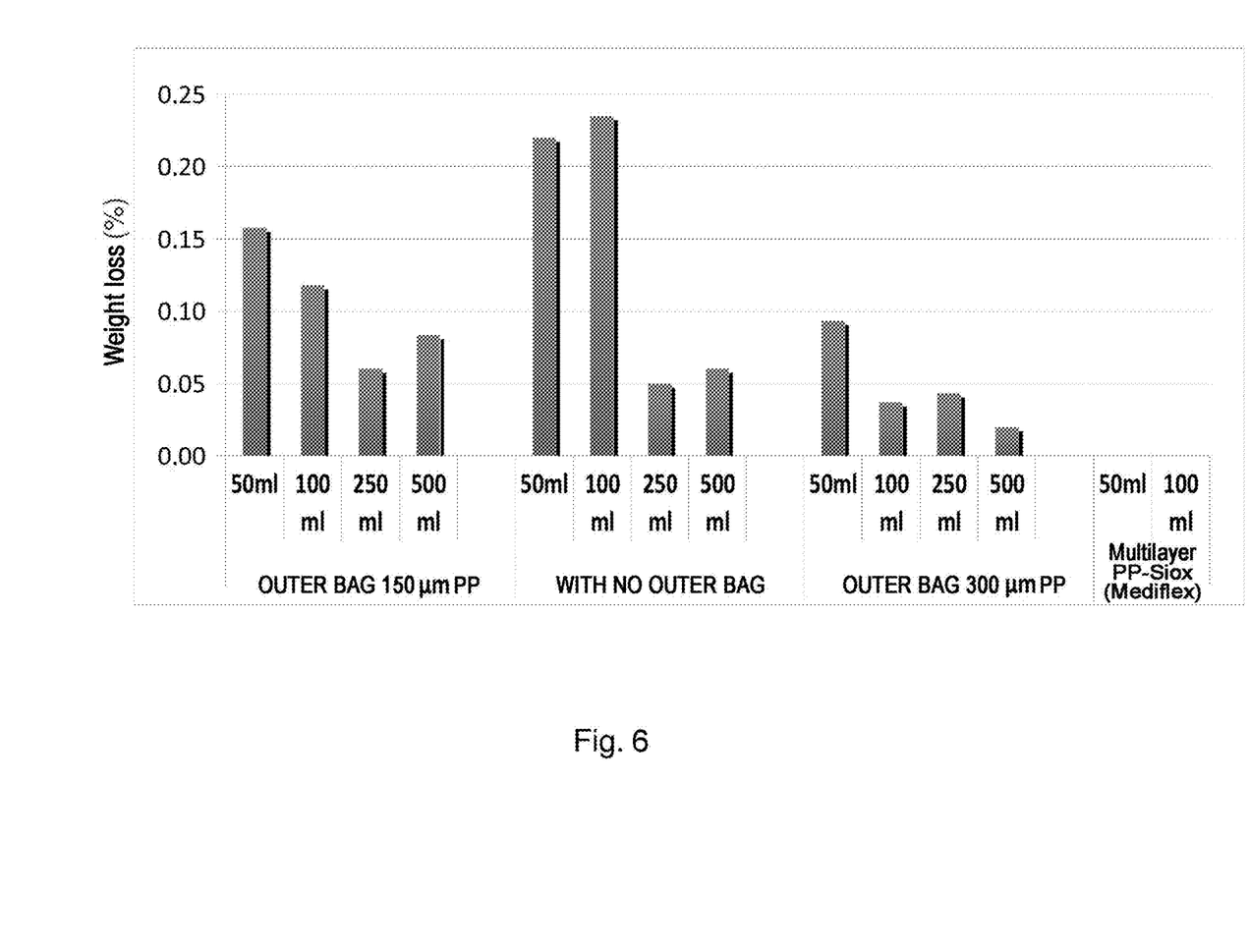
FIG. 6 shows the results for weight loss in a stability study (12 months at 5° C.) of a primary bag which contains a solution of human plasma albumin without a secondary bag and with different secondary containers: 150 µm thick polypropylene (PP), 300 µm thick polypropylene (PP) and polypropylene coated with silicon oxides (multilayer PP-SiOx).
Figure 7:
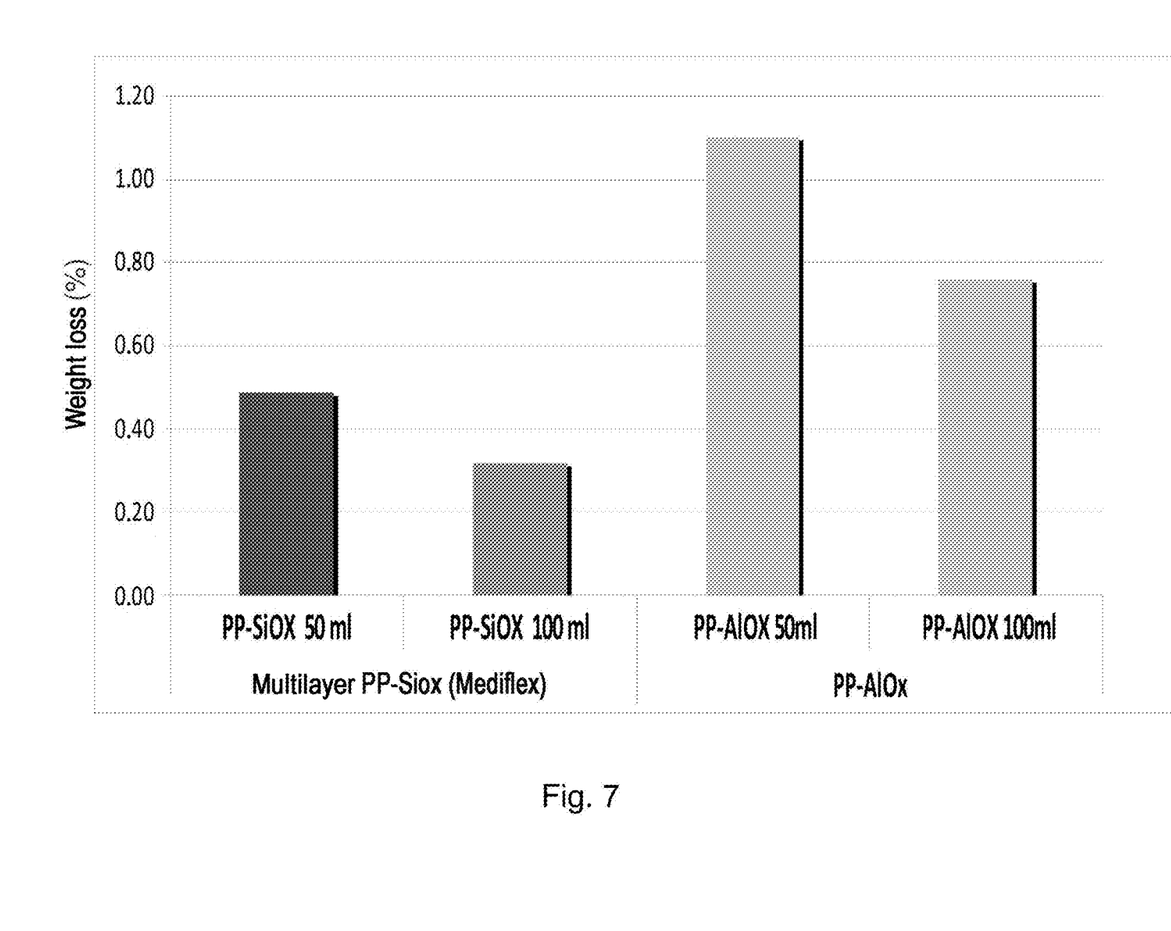
FIG. 7 shows the results for weight loss in an accelerated stability study (2 months at 40° C.) of a primary bag which contains a solution of human plasma albumin with secondary bags of polypropylene coated with silicon oxides (multilayer PP-SiOx) and polypropylene covered with aluminium oxides (PP-AlOx).

The results can be seen in FIG. 5. A reduction is observed in the weight loss of the primary bags which were placed in secondary bags made of multilayer PP-SiOx (MEDIFLEX, Amcor, Belgium) compared with secondary bags made of PP-AlOx.

Example 4. Stability Study of a Container According to the Present Invention which Contains Immunoglobulins Three containers according to the present invention were prepared (SOLMED Infuflex 9190/MEDIFLEX PP-SiOx) which contained a 10% solution of human immunoglobulins for intravenous use, similar to that marketed under the name Gamunex® (Grifols S.A, Spain). Said containers were kept at 5° C. for three months and different parameters were compared with the same immunoglobulin solution but packed in glass vials (n=6) at the beginning (T=0) and at the end of three months. The results are shown in Table 1.

TABLE 1

Results of the stability study of the container of the present invention compared with glass vials with immunoglobulins at 5° C. for three months

| Parameter | IGIV in containers n = 3 | | IGIV in glass vials n = 6 |
|---|---|---|---|
| | t = 0 | 3 months | 3 months |
| Appearance | Correct | Correct | Correct |
| pH | 4.1-4.2 | 4.2 | 4.1-4.2 |
| Turbidity (NTU) | 2.6-3.3 | 2.5-2.7 | n.a. |
| Osmolality (mOsm/kg) | 256-261 | 258-263 | n.a. |
| Molecular Distribution | | | |
| Polymers and aggregates | 0.1-0.2 | 0.1-0.3 | <1 |
| Dimers + monomers | 99.1-99.3 | 98.9-99.2 | 100 |
| Weight loss (%) | 0.00 | 0.01-0.04 | n.a. | n.a.: not analysed

As can be seen in Table 1, all the parameters measured meet the specifications of the European Pharmacopoeia and the United States Pharmacopoeia for three months at 5° C.

Example 5. Accelerated Stability Study of a Container According to the Present Invention which Contains Immunoglobulins Three containers according to the present invention were prepared (SOLMED Infuflex 9190/MEDIFLEX PP-SiOx) which contained a 10% solution of human immunoglobulins for intravenous use, similar to the one marketed under the name Gamunex® (Grifols S.A, Spain). Said containers were kept at 30° C. for three months and different parameters were compared with the same immunoglobulin solution but packed in glass vials (n=6) at the beginning (T=0) and at the end of three months. The results are shown in Table 2.

TABLE 2

Results of the accelerated stability study of the container of the present invention compared with glass vials with immunoglobulins at 30° C. for three months

| Parameter | IGIV in containers n = 3 | | IGIV in glass vials n = 6 |
|---|---|---|---|
| | t = 0 | 3 months | 3 months |
| Appearance | Correct | Correct | Correct |
| pH | 4.1-4.2 | 4.2 | 4.1-4.3 |
| Turbidity (NTU) | 2.6-3.3 | 2.6 | n.a. |
| Osmolality (mOsm/kg) | 256-261 | 257-267 | n.a. |
| Molecular distribution | | | |
| Polymers and aggregates | 0.1-0.2 | 0.3-1.1 | 0-1 |
| Dimers + monomers | 99.1-99.3 | 96.1-97.0 | 96-97 |
| Weight loss (%) | 0.00 | 0.19-0.21 | n.a. | n.a.: not analysed

As can be seen in Table 2, all the parameters measured meet the specifications of the European Pharmacopoeia and the United States Pharmacopoeia for three months at 30° C.

Example 6. Color Stability Study of an Immunoglobulin Solution Packed in the Container According to the Present Invention In addition to the parameters measured in Examples 4 and 5 above, the color (optical density at 350-500 nm) of the immunoglobulin solution was determined in both stability studies and in the glass vials. As explained above, the color of the intravenous immunoglobulin solution must meet the requirement imposed by the European Pharmacopoeia, that is, the solution must be clear and of a pale yellow to light brown color. The results obtained are shown in Table 3.

TABLE 3

Results for optical density ($OD_{350-500\ nm}$) in the 10% immunoglobulin stability studies

| Receptacle | t = 0 (n = 3) | 3 months at 5° C. (n = 3) | 3 months at 30° C. (n = 3) |
|---|---|---|---|
| Containers | 0.0504-0.0542 | 0.0540-0.0572 | 0.1013-0.1210 |
| Glass vials | n.a. | 0.0526-0.0587 | 0.1229-0.1557 |

As can be seen, the color in the container of the present invention is comparable to the color obtained in the glass vials.

Although the invention has been described with respect to examples of preferred embodiments, said examples should not be considered to limit the invention, which will be defined by the widest interpretation of the following claims.

What is claimed is:

1. A container for a solution of human plasma proteins, comprising:
   a) a primary inner bag comprising a first multilayer polymer film, wherein the first multilayer polymer film comprises two outer layers of polyethylene (PE) and an intermediate layer of ethylene vinyl alcohol (EVOH) copolymer, and
   b) a secondary outer bag comprising a second multilayer polymer film, wherein the second multilayer polymer film comprises layers of polyethylene terephthalate (PET)-silicon oxides (SiOx), oriented polyamide (OPA), polypropylene (PP)-silicon oxides (SiOx) and polypropylene (PP).

\* \* \* \* \*